(12) United States Patent
Kashani et al.

(10) Patent No.: US 8,649,008 B2
(45) Date of Patent: Feb. 11, 2014

(54) COMBINED SPECTRAL AND POLARIMETRY IMAGING AND DIAGNOSTICS

(75) Inventors: Amir H. Kashani, Los Angeles, CA (US); Mark S. Humayun, Glendale, CA (US)

(73) Assignees: University of Southern California, Los Angeles, CA (US); Doheny Eye Institute, Los Angeles, CA (US)

( * ) Notice: Subject to any disclaimer, the term of this patent is extended or adjusted under 35 U.S.C. 154(b) by 0 days.

(21) Appl. No.: 13/021,524

(22) Filed: Feb. 4, 2011

(65) Prior Publication Data

US 2011/0206291 A1  Aug. 25, 2011

Related U.S. Application Data

(60) Provisional application No. 61/301,409, filed on Feb. 4, 2010.

(51) Int. Cl.
*G01J 3/28* (2006.01)
*G01J 3/447* (2006.01)
*A61B 3/14* (2006.01)

(52) U.S. Cl.
USPC ........... 356/327; 356/328; 356/326; 356/322; 351/206

(58) Field of Classification Search
USPC ........................................ 356/327
See application file for complete search history.

(56) References Cited

U.S. PATENT DOCUMENTS

| | | | |
|---|---|---|---|
| 4,564,761 A | 1/1986 | Buckwald et al. | |
| 4,836,207 A | 6/1989 | Bursell et al. | |
| 5,097,135 A * | 3/1992 | Makino et al. ............. 250/461.1 | |
| 5,166,052 A | 11/1992 | Cercek et al. | |
| 5,539,517 A | 7/1996 | Cabib et al. | |
| 5,782,770 A | 7/1998 | Mooradian et al. | |
| 5,784,162 A | 7/1998 | Cabib et al. | |
| 5,822,035 A | 10/1998 | Bille | |
| 5,835,214 A | 11/1998 | Cabib et al. | |

(Continued)

FOREIGN PATENT DOCUMENTS

| | | |
|---|---|---|
| JP | 2003-010133 A | 1/2003 |
| JP | 2004-267616 A | 9/2004 |
| JP | 2008-188139 A | 8/2008 |
| WO | 2011/097508 A2 | 8/2011 |

OTHER PUBLICATIONS

Bonifacio, A. et al. 2008. Spatial distribution of heme species in erythrocytes infected with Plasmodium falciparum by use of resonance Raman imaging and multivariate analysis. Anal Bioanal Chem. Dec. 2008; 392(7-8):1277-82. (Epub Oct. 5, 2008.).

(Continued)

*Primary Examiner* — Tarifur Chowdhury
*Assistant Examiner* — Sunghee Y Gray
(74) *Attorney, Agent, or Firm* — McDermott Will & Emery LLP (57) ABSTRACT

Combined spectral and polarimetry imaging and diagnostic techniques are disclosed, including an imaging system that simultaneously records spatially co-registered spectral and polarization information from an image of a target scene such as an ocular structure or material or device in an around the eye. Image acquisition and image calibration by such an imaging system or an imaging spectrometer or polarimeter are also disclosed. Methods of data storage and image display relevant to medical practice in general and ophthalmology practice specifically are further disclosed.

43 Claims, 8 Drawing Sheets

(56) References Cited

U.S. PATENT DOCUMENTS

| | | | |
|---|---|---|---|
| 5,856,871 A | 1/1999 | Cabib et al. | |
| 5,991,028 A | 11/1999 | Cabib et al. | |
| 6,142,629 A | 11/2000 | Adel et al. | |
| 6,403,332 B1 | 6/2002 | Bearman et al. | |
| 6,480,333 B1 | 11/2002 | Maker et al. | |
| 6,522,403 B2 | 2/2003 | Wilson et al. | |
| 6,556,853 B1 | 4/2003 | Cabib et al. | |
| 6,574,490 B2* | 6/2003 | Abbink et al. | 600/316 |
| 6,665,556 B1 | 12/2003 | Alfano et al. | |
| 6,683,455 B2 | 1/2004 | Ebbels et al. | |
| 6,690,817 B1 | 2/2004 | Cabib et al. | |
| 6,704,106 B2 | 3/2004 | Anderson et al. | |
| 6,750,036 B2 | 6/2004 | Bearman et al. | |
| 6,750,964 B2 | 6/2004 | Levenson et al. | |
| 7,034,938 B1 | 4/2006 | Miles et al. | |
| 7,113,814 B2 | 9/2006 | Ward et al. | |
| 7,126,676 B2 | 10/2006 | Greco | |
| 7,188,951 B2 | 3/2007 | Okinishi | |
| 7,217,518 B2 | 5/2007 | Sekar et al. | |
| 7,299,080 B2 | 11/2007 | Acosta et al. | |
| 7,471,831 B2 | 12/2008 | Bearman et al. | |
| 7,532,325 B2* | 5/2009 | Ahmed et al. | 356/327 |
| 7,612,880 B2 | 11/2009 | Chipman | |
| 7,768,641 B2* | 8/2010 | Bearman et al. | 356/328 |
| 7,876,434 B2 | 1/2011 | Wilson et al. | |
| 7,967,016 B2* | 6/2011 | Anderson et al. | 128/898 |
| 2004/0189937 A1 | 9/2004 | Okinishi | |
| 2007/0165223 A1 | 7/2007 | Wilson et al. | |
| 2008/0019921 A1* | 1/2008 | Zhang | 424/9.6 |

OTHER PUBLICATIONS

Demirev, P.A. et al. 2002. Detection of malaria parasites in blood by laser desorption mass spectrometry. Anal Chem. Jul. 15, 2002; 74(14):3262-6.

Egan, T.J. et al. 1994. Quinoline anti-malarial drugs inhibit spontaneous formation of beta-haematin (malaria pigment). FEBS Lett. Sep. 19, 1994; 352(1):54-7.

Fawzi, A.A. et al. 2008. Snapshot Retinal Oximetry: Results of a Novel Four Wavelength Oximetry Formula in Retinal Hyperspectral Imaging. ARVO Meeting Abstracts, Apr. 11, 2008; 49: 897.

Francis, S.E. et al. 1997. Hemoglobin metabolism in the malaria parasite Plasmodium falciparum. Annu Rev Microbiol. 1997; 51:97-123. Review.

Frosch, T. et al. 2007. In situ localization and structural analysis of the malaria pigment hemozoin. J Phys Chem B. Sep. 20, 2007; 111(37):11047-56. (Epub Aug. 25, 2007).

Johnson, W.R. et al. 2007. Snapshot hyperspectral imaging in ophthalmology. J Biomed Opt. Jan.-Feb. 2007; 12 (1):014036.

Kashani, A.H. et al. 2009. Snapshot Hyperspectral Imaging: Retinal Oxygen Saturation Analysis From Hyperspectral Images of Rabbit Retina. ARVO Annual Meeting Abstract, Apr. 11, 2009, Program 50:1404.

Kashani, A.H. et al. 2010. Spectral Determination of Retinal Oxygen Content in Dog Retina Using Computerized Tomographic Imaging Spectroscopy. ARVO Meeting Abstracts, Apr. 11, 2010, Program 51:5768.

Kashani, A.H. et al. 2011. Measurements of Intravascular Oxygen Saturation Gradients and Arteriovenous Gradients: A Study Using Hyperspectral Imaging Computed Tomographic Spectroscopy. ARVO Annual Meeting Paper Presentation Apr. 22, 2011 Program 52:1247.

Ong, C. W. et al. 1999. Resonance Raman Microspectroscopy of Normal Erythrocytes and Plasmodium berghei-Infected Erythrocytes. Applied Spectroscopy, 53(9):1097-1101.

Webster, G.T. et al. 2009. Discriminating the intraerythrocytic lifecycle stages of the malaria parasite using synchrotron FT-IR microspectroscopy and an artificial neural network. Anal Chem. Apr. 1, 2009; 81(7):2516-24.

Locke, A.M. et al. 2002. Snapshot Imaging Spectropolarimeter. Proceedings SPIE, vol. 44, No. 81, pp. 64-72.

International Search Report and Written Opinion of the International Searching Authority, dated Sep. 27, 2011, for PCT Application No. PCT/US2011/023786, filed Feb. 4, 2011, published Aug. 11, 2011 as WO 2011/097508A2, entitled "Combined Spectral and Polarimetry Imaging and Diagnostics."

* cited by examiner

COMBINED SPECTRAL AND POLARIMETRY IMAGING AND DIAGNOSTICS

CROSS-REFERENCE TO RELATED APPLICATION

This application is based upon and claims priority to U.S. Provisional Patent Application No. 61/301,409, entitled "Spectral Imaging of the Eye for Diagnosis of Disease States," filed 4 Feb. 2010, client reference no. 10-185, the entire content of which are incorporated herein by reference.

STATEMENT REGARDING FEDERALLY SPONSORED RESEARCH

This invention was made with government support under Grant No. EEC0310723 awarded by the National Science Foundation. The government has certain rights in the invention.

BACKGROUND

Spectroscopic analysis may be used to analyze biological tissues in vivo and in vitro. Recording and analysis of spectral signals from tissue can provide detailed information regarding the physical composition of the target tissue as well as the state of individual physical components. Many molecules may have unique spectral signatures. For example hemoglobin may have distinct spectra depending on its oxygenation. The difference in the spectra between oxy- and deoxy-hemoglobin has been used in multispectral and hyperspectral methods to determine the oxygen content of retinal arteries and veins.

Some described methods and instruments may be limited by the need to manually adjust settings, slow acquisition times, limited field-of-view, poor spatial and/or spectral resolution and insufficient spectral range. In addition, spectral signals, may be subject to deleterious optical effects such as diffraction, absorption, contaminating emissions and scatter by any material in the light path between the illumination source and recording apparatus. Variations in background or surrounding tissue pigmentation can affect the spectroscopic profile of a target since most tissues are semi-transparent. In the case of the retina, recording spectral information may be confounded by the effects of a number of different tissues that encounter the light going into and coming out of the retina. These tissues may include the tear film, cornea, aqueous humor, iris, lens, lens capsule, vitreous, and vitreous debris (red blood cells, white blood cells, cellular debris, vitreous syneresis), choroicapillaris, choroid, Bruch's membrane, and retinal pigment epithelium (RPE). Collectively, one or more of these tissues contribute "spectral noise" to the signal of interest. "Spectral noise" is used herein to mean any spectral information that is not from or due to the target of interest. For example, cataracts, corneal opacities, intraocular inflammation, vitreous hemorrhage, lens dislocation and epiretinal membranes can significantly alter the spectral profile of any light going into or coming out of the retina.

Polarization is a property of electromagnetic waves that describes the orientation of their oscillations. The orientation of the electric fields of electromagnetic waves emanating from a surface may or may not be correlated resulting in various states of polarization. Measurement of these polarization states has provided useful information regarding some biological targets. Analysis of polarization anisotropy in tissue structures has been limited because of the technical limitations in polarimetry. In the eye, the largest retardance is associated with the cornea although the lens and vitreous also contribute. Structures with the most regular microstructures such as the corneal stroma, nerve fiber layer (NFL), Henle's nerve fiber layer, scleral crescent at optic nerve head, lamina cribrosa, rod and cone photoreceptors, Bruch's membrane and sclera are most likely to generate non-depolarizing polarization. The cornea, NFL and Henle's NFL have demonstrated the most prominent polarization properties. Recently the development of commercial polarimeters has made possible the study of tissue anisotropy in the retina. Such polarimeters are incomplete, however, and do not measure all forms of polarization behavior (e.g., depolarization, diattenuation, and retardance).

Despite the advancement noted in polarimetry, limitations still remain. For example, typical polarimeter instruments are commonly limited by the need to manually adjust settings, slow acquisition times, limited field-of-view, and insufficient dynamic range. A relatively small field-of-view and a long acquisition time can necessitate significant effort in image registration and analysis. In addition, polarization of light is also subject to the same sources of noise as described above for spectral imaging. These limitations likely place an upper limit on the clinical sensitivity and specificity of commercial polarimeters and other polarization measurements.

In the medical sciences, diagnostic technologies based on spectral imaging and polarimetry are relatively few and generally not well accepted in the ophthalmology community for multiple reasons. First, these imaging technologies are not well adapted to clinical use because of long image acquisition times, small field-of-view, poor spatial and/or spectral resolution, limited spectral range and incompatibility with other medical equipment. Second, even in cases where images are acquired there may be no reliable method by which to effectively calibrate spectral or polarization data for the sources of noise as described above. Therefore images commonly vary from one exam to the next and the exact source of the spectral or polarization signals is not clear because of the many sources of noise described above. This can limit the clinical utility of the devices as longitudinal follow-up is important in characterizing the progression or regression of a disease process.

SUMMARY

Simultaneous, spatially colocalized (or spatially coregistered) spectral and polarimetry data acquisition and image processing may be applied for biological research and/or medical diagnostics including retinal diagnostics and therapeutics. An imaging system may simultaneously record spatially co-registered spectral and polarization information from an image of a target scene, e.g., a retina. Ocular structure and retinal image acquisition and retinal image calibration may be facilitated by such an imaging system or any imaging spectrometer, polarimeter or combinations thereof. Data storage and image display may be used for medical practice in general and ophthalmology practice specifically.

Examples of systems and methods are disclosed for acquiring and analyzing spatially co-localized spectral and polarization data from a sample or subject, e.g., the human eye.

Further examples of systems and methods are disclosed for calibrating images of a sample or subject, e.g., the human eye, to remove deleterious optical effects.

These, as well as other components, steps, features, objects, benefits, and advantages of the present disclosure, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it refers to the same or like components or steps.

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings:

FIGS. 1A-1B depict an example of a combined imaging spectrometer-polarimeter system; FIG. 1A depicts components of a computed tomography imaging system utilized for the system; FIG. 1B depicts components of a polarimeter utilized for the system;

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

An imaging system that simultaneously records spatially co-registered spectral and polarization information from an image of a target scene, e.g., an ocular structure and tissues such as a retina or an object in or around the eye such as a medical device or material. Image acquisition and image calibration, e.g., of ocular structures, tissues, and objects, may be facilitated by such an imaging system or any imaging spectrometer, polarimeter or combinations thereof. Data storage and image display may be relevant to and used for medical practice in general and ophthalmology practice specifically.

Hyperspectral imaging may use 2-dimensional dispersion optics such as diffraction gratings in conjunction with a polarimeter and computed tomographic imaging spectroscopy (CTIS).

CTIS technology according to the present disclosure can overcome many previously-observed obstacles to clinical application. A CTIS system can capture coregistered spatial and spectral information by imaging a target area or location through or across a two-dimensional (2D) grating that produces multiple spectrally dispersed images, which can be recorded by a focal plane array. A polarimeter can be used in conjunction with the CTIS system to simultaneously obtain spatially coregistered data about the polarization attributes of the image. A CTIS based camera can be mounted on a standard fundus camera and acquire images containing, e.g., approximately 50 wavelengths of spectral data in a relatively short amount of time (a "snapshot, e.g., <3 msec). Consequently, hyperspectral images may be only minimally blurred by movement, e.g., microsaccades, or eye movements, and do not need image registration to eliminate motion artifact or pixel misregistration. Data acquisition can be accomplished using standard photography, e.g., fundus photography which has been in clinical practice for decades. Data can be collected on a computer using standard image acquisition software. Computed tomographic algorithms can be used to reconstruct the spectrally dispersed images into a "hyperspectral cube" of spectral and spatial information that can be probed for wavelength information.

Figure 1A:
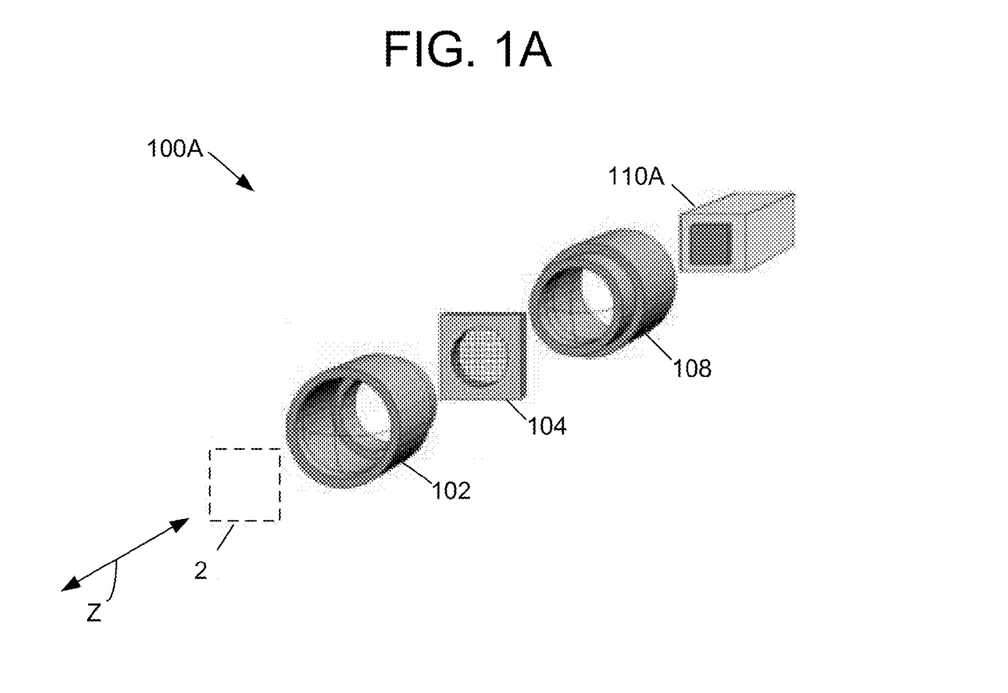
Figure 1B:
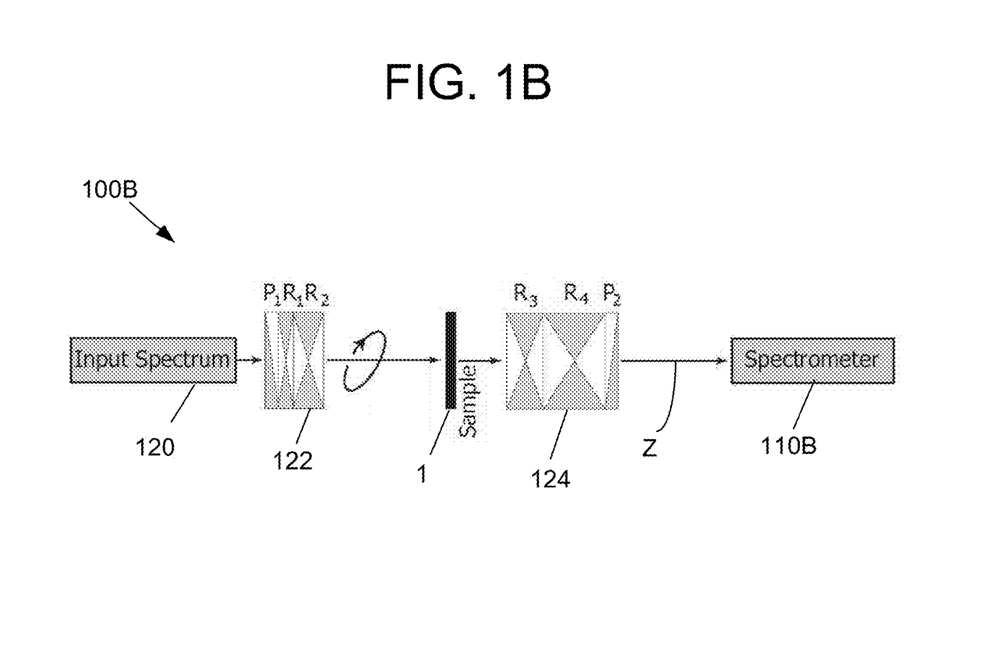

FIGS. 1A-1B depict an example of an imaging spectrometer-polarimeter system 100. FIG. 1A depicts components of a computed tomography imaging spectrometer (CTIS) 100A utilized for the system 100, while FIG. 1B depicts components of a polarimeter 100B utilized for the system 100. As illustrated in FIG. 1A, a CTIS system 100A simultaneously captures spatial and spectral information of an image 2 (e.g., of a retina) by imaging the scene through a two-dimensional grating disperser (also referred to as a dispersion element or diffractive optical element) 104. A collimating lens 102 can be used to collimate the image before encountering the dispersion element 104. The diffractive optical element 104 can operate at multiple orders, creating an array of images on the sensor. A primary lens 108 can facilitate focusing of the image on a detector 110A. Any suitable detector may be used. Examples include, but are not limited to focal plane array (FPA) detectors configured to detect light intensity at wavelengths in the visible, infrared (IR), and/or ultraviolet (UV) spectrums. In exemplary embodiments, a digital color CCD (Qimaging© Retiga 4000R) may be used as the detector. Imposing spatial or spectral modulation on the image scene can significantly improve the spectral reconstructions. Accordingly, color filters used on the camera detector elements (e.g., 110A) that provide each RGB plane can act to provide spectral modulation. The dispersion effect on the image 2 by the dispersion element 104 can produce multiple, spectrally dispersed images of the original image 2 (e.g., retina) that can be recorded, e.g., by focal plane array (FPA) detector 110A. Optical axis Z is shown to indicate the propagation of light forming the image 2 from a target region. Optical axis Z can pass through other optical components/systems prior to reaching the focal plane array 110 as described below for FIG. 1B.

The recorded intensity pattern can be stored and/or provided to a suitable processing system for image processing. From the captured intensity pattern, computed-tomography algorithms may be used to reconstruct the scene into a "cube" of coregistered spatial (x and y) and spectral/polarization (wavelength, or frequency domain) information. The image cube in wavelength space can then reconstructed from a single image. In exemplary embodiments, the basic CTIS design uses just two lenses and a focal plane detector in addition to an image forming system (including but not limited to a fundus camera). Any suitable image forming system may be used.

FIG. 1B depicts components of a polarimeter 100B utilized for the system 100. Polarimeter 100B can include an illumination source 120 producing light with a desired illumination spectrum. Groups of polarizers and retarders, 122 and 124, are shown bracketing the sample 1, and include polarizers (shown as P1-P2) multiple thin retarders, indicated by R1-R4, have desired orientations of fast and transmission axes. A polarizer or functional equivalent can be an integrated unit or separate components that function as a polarimeter. In one potential embodiment, the polarimeter function may be achieved by use of a polarization sensitive diffraction grating. The light from the sample can be recorded by spectrophotometer 110B. Corresponding data of the captured image can be provided to a processing system, e.g., for image processing and/or storage and/or calibration. In exemplary embodiments, retarders R1 and R4 have their fast axes oriented at 45°, retarders 2 and 3 at 0° while polarizers P1 and P2 both have their transmission axes oriented at 0°. Of course while a transmission optical path is shown, polarizer 100B can be used with a reflectance mode, e.g., when imaging a retina in vivo. In exemplary embodiments, image data from the spectrometer 110B is spatially and temporally co-registered with the image data received from FPA detector 110A in FIG. 1 to facilitate further techniques of the disclosure, as described in further detail below.

Polarimeter 100B can be utilized for channeled spectropolarimetry for performing spectrally-resolved Stokes polarimetry measurements. By taking advantage of the property of thick retarders (122 and 124) that the retardance varies rapidly with wavelength, polarimeter 100B can provide for placement of various polarization parameters onto differing carrier frequencies in the Fourier (OPD) domain. Filtering the measured spectrum's Fourier transform data (the "OPD spectrum") can then be used to obtain the estimated polarization spectra. The sample 1 (e.g., a retina) can thus be illuminated by a polarization state which varies spectrally, allowing a simultaneous measurement of the output polarization states of the sample for many input polarization states. If the Mueller matrix of the sample varies only slowly with wavelength, then the measurements will not overlap in the OPD domain and can be accurately recovered.

It should be noted that systems 100A and 100B shown in FIGS. 1A and 1B, respectively, are shown separate for ease of explanation and understanding. Systems 100A and 100B may actually be combined in an integrated unit. In exemplary embodiments, FPA 110 and spectrometer are integrated with one another or share common detector elements, e.g., the same charge-coupled device (CCD) FPA. In this embodiment, the single FPA would have a system calibration matrix that would include spectral and polarization properties of incident light on the FPA. Additional exemplary embodiments of this device can be reasonable envisioned. For example, one other embodiment may include addition of a beamsplitter and two focal plane arrays where one FPA is used only for detecting spectral data and the other FPA only for polarization states. In this case, each FPA would have a unique but inter-related system calibration matrix to allow for spatial colocalization of spectral and polarization data In exemplary embodiments, the specific type of diffractive optical element 104 used is a computer-generated hologram (CGH), e.g., in accordance with those shown an described in U.S. Pat. No. 7,876,434, U.S. Pat. No. 6,522,403, and/or U.S. Pat. No. 5,782,770, the entire contents of all of which are incorporated herein by reference. Development of techniques for fabricating the grating with electron-beam lithography has been the main driver in the development of this instrument. The CGHs may be composed of cells of square pixels (e.g., 8×8 pixels/cell) that are arrayed to form a 2-D grating. The pixel depths may be designed using a CTIS-specific iterative optimization algorithm such that the dispersion order intensities are nearly equal after distribution across the focal plane array. This can maximize the overall system signal-to-noise ratio by avoiding saturation in a single diffraction order. An analog direct-write electron-beam lithography technique was developed to accurately fabricate a CGH. This technique requires only a single exposure followed by iterative development. It allows the production of fine-featured analog surface-relief profiles in thin films of E-beam resist with a depth error less than 5%. As noted previously, the diffractive optic element can be a transmissive type element or a reflective type element.

For tomographic image reconstruction, e.g., from a dispersed image recorded at detector 110, a calibration matrix may be used. Such a calibration matrix can be obtained by measuring the location on the image plane of pixels from the object plane at different wavelength with a movable fiber optic coupled to a monochromator. The efficiencies, spot centroids, and point spread functions of all the diffraction orders can be measured at all wavelengths in the operating band. This data can be used to build a "system transfer matrix" of field-stop-to-detector or entrance-aperture-to-detector connection coefficients. Once the system transfer matrix is known, the images (e.g., of the retina) can be reconstructed to obtain their spectra. The iterative expectation-maximization (EM) reconstruction algorithm may be used in exemplary embodiments. This algorithm was developed for reconstructing positron-emission tomography medical images but other emission tomography algorithms are applicable as well. This estimation approximates the spatial and spectral information using voxel basis functions, which define the solution space for accurate reconstructions. The reconstruction may start with an initial condition for the image (scene) which results in a predicted detector image. Corrections can then be made to the image (scene) based on back projection of the ratio of the measured detector image and predicted detector images. This process can be repeated iteratively until the predicted detector image matches the measured detector image to a desired error tolerance. Typically 10 to 20 iterations may be expected for good image reconstructions. In another embodiment, the multiplicative algebraic reconstruction algorithm (MART) can similarly be used.

Exemplary embodiments of system 100 may be used to provide and/or process, e.g., calibrate, images of structures, tissues, objects, and/or optical media in and around the eye. Such structures or optical media may include but are not limited to tear film, cornea, aqueous humor, lens and lens capsule, vitreous humor, and internal limiting membrane; they can also include interstitial spaces (in the case of edema), an intraocular foreign body, an implanted device in the eye (e.g., a medical device such as a retinal prosthesis), an intraocular mass, a surgically placed material, a biological tissue, a fluorescently or chromatically labeled material or materials, and nanoparticles such as injected nanoparticles, and/or dyes, to list a few. Other structures or optical media may be imaged and process, e.g., calibrated, within the scope of the present disclosure.

Figure 2A:
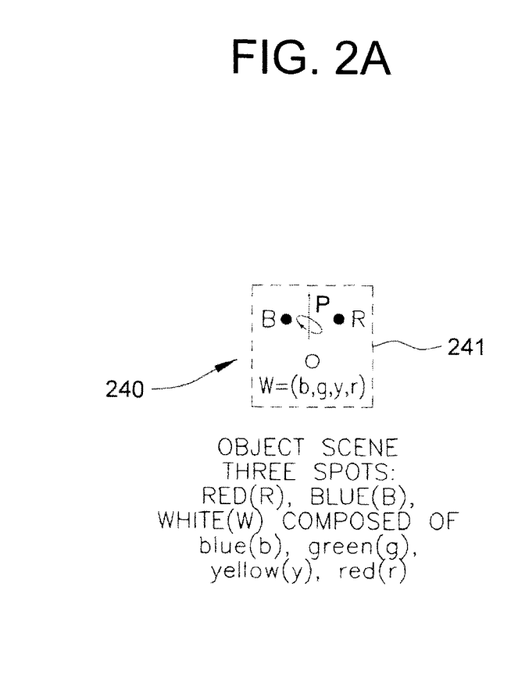
FIGS. 2A-2B depict a representative image and dispersion effects of the image after propagation along an optical axis from a 2D dispersion element.
Figure 2B:
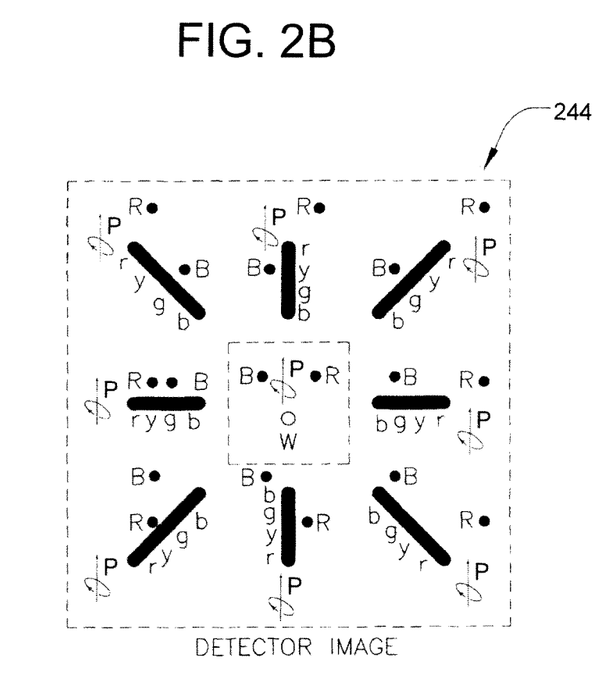

FIGS. 2A-2B show how the various orders are dispersed across the focal plane as well as spectra derived for an image scene. Image 240 (including separate red, white, and blue dots) is shown with a boundary 241. Image 240 also includes a polarization, P, as indicated (with adjoining symbol). The dispersion pattern 244, with an array of multiple dispersed images, is shown in FIG. 2B. Skewing effects based on color (wavelength) are noticeable. It may be noted that each image is not simply composed of single wavelengths; spatial, spectral and polarization information from each object pixel is multiplexed over the entire array. Hence, a single image contains all the information required to reconstruct the spectral and polarization image states. Note that there is a zero-order image for focusing—a difficult task for many spectral imagers. As shown in FIG. 2B, each diffracted order includes a polarization P. While only one polarization symbol is included here for simplicity, we intend this to represent a partial or complete characterization of the polarization properties of the target tissue (or object) as allowed by the optical elements in a given imaging system. For example, in one potential embodiment if a diffractive optical element is used that produces dispersion as a function of polarity (in addition to wavelength), a different polarity state may be present for different diffracted orders.

Figure 3:
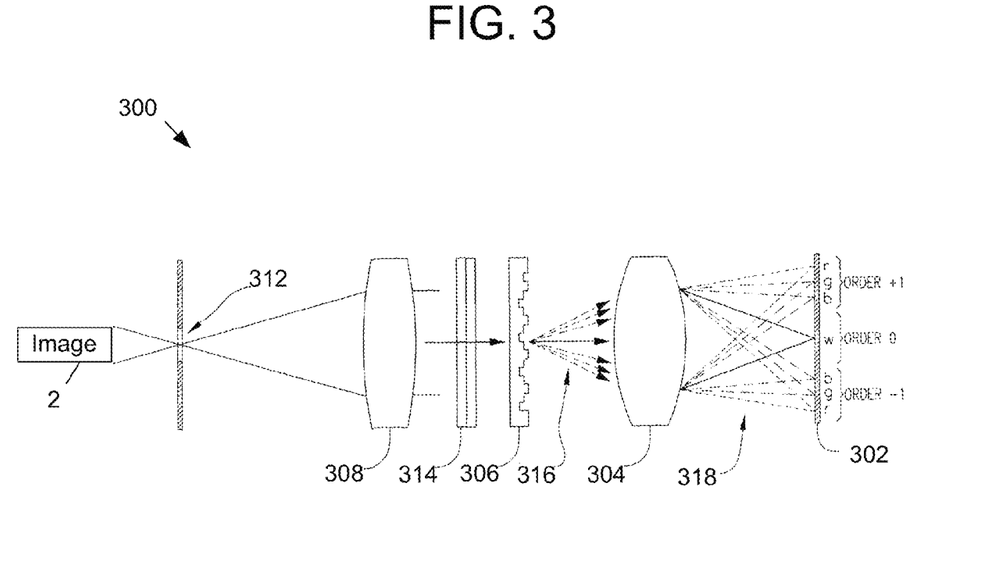
FIG. 3 depicts a cross section of an example of a combined imaging spectrometer-polarimeter system producing dispersion of an image.

FIG. 3 depicts the general optical layout of a combined imaging spectrometer-polarimeter system 300 in accordance with exemplary embodiments. In operation, a primary optical system (such as a telescope, microscope, endoscope, etc.) forms a real image of the scene on a rectangular aperture 312 serving as a field stop 312 shown in FIG. 3. Light in the field stop 312 is collimated by collimating lens 308, filtered through a wide-band filter means 314 and passed through the 2D grating disperser 306, which produces a 2D array of diffraction orders 316. The imaging (primary) lens 304 then re-images the diffraction orders of light 318 onto the FPA detector 302 which records the intensity of the incident light. Each diffraction order 318 transmitted from the 2D grating disperser 306 produces a spectrally dispersed image, except for the undiffracted "zeroth" order which produces an undispersed image in the center of the FPA detector 302. An image 2 is shown entering the system 300 passing through a filter 314 and being dispersed (shown by 316) due to the diffractive effects of grating disperser 306. Collimating lens 304 is shown focusing (shown by 318) the different orders of the diffracted image on detector 302.

Color FPA detector 302 can take a number of forms. For example, in one embodiment, the color FPA detector 302 may comprise a digital color camera including a digital image sensor, such as a Foveon X3®, digital image sensor or a Bayer color filter mosaic. The Foveon X3® digital image sensor includes three layers of pixels (i.e. one red layer, one blue layer and one green layer) on top of each other embedded in a silicon sensor. The Bayer color filter mosaic includes a single layer of a repeating array of red, green and blue filter material deposited on top of each spatial location, and the Bayer color filter mosaic uses twice as many green filters as red or blue filters. In another embodiment, the color FPA detector 302 may include three charge coupled devices ("CCDs"), one for each color: red, green and blue. In other embodiments a reflective disperser or diffractive optical element may be used. Reflective, as opposed to refractive, dispersers may be preferable for some situations as absorption and dispersion effects of the optical medium of the optical element can be mitigated or eliminated. Suitable examples are shown and described in U.S. Pat. No. 7,878,434, the entire content of which is incorporated herein by reference. In exemplary embodiments, a field stop aperture 312 can be employed in the optical train to facilitate definition of the field of view (FOV) of the system 300. According to an exemplary embodiment, recovered spectra are improved by using a color camera in place of the traditional monochrome camera. A color camera can be used in place of the monochrome camera in both transmissive and reflective CTIS systems. Alternatively, multiple monochromatic cameras can be used with appropriate system transfer matrices for spectral and polarization components of the image.

In still another embodiment, the detector 302 may include or be part of any suitable device, such as a monochrome camera or a color camera, over which is positioned a transmission filter that performs a user-defined transmissive function. For example, a color filter adapted to transmit a single color (e.g. red, green or blue) can be positioned over the FPA detector. Step or graded filters, polarizers and/or retarders may also be used.

Figure 4:
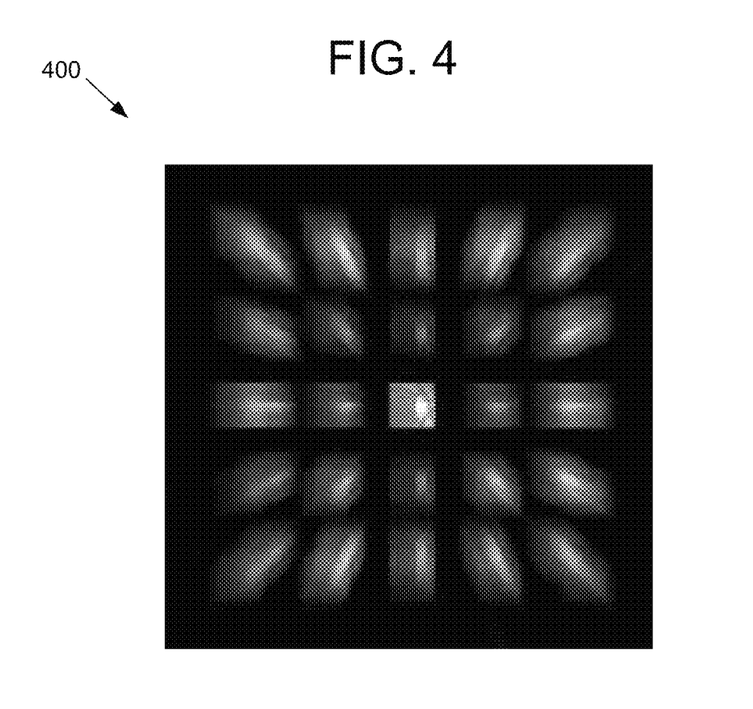
FIG. 4 is a photograph of a raw image showing dispersion of an image of a optic disk and surrounding vascular structure.

FIG. 4 shows a raw image 400 from an imager (e.g., system 300 of FIG. 3) of an optic disk and surrounding vascular structure. The field of view indicated is 12 degrees (30-degree fundus camera setting). The maximum field of view obtained with the system was 18 degrees, which is enough to show the macula and optic disk in one shot. Note the radial dispersion of the image.

Figure 5:
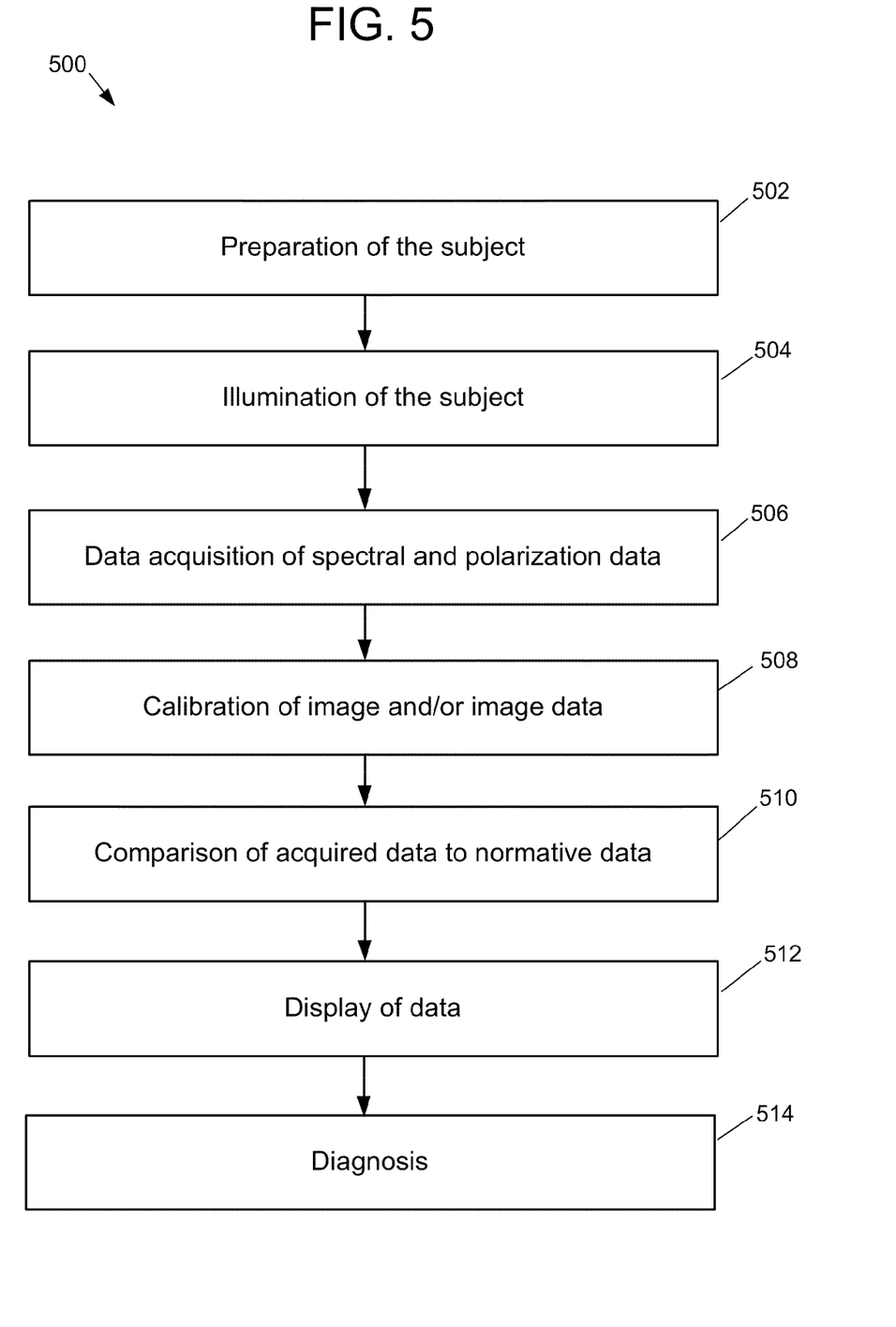
FIG. 5 depicts a flow chart of an example of a method of combined spectral and polarimetry imaging.

FIG. 5 depicts a flow diagram of a method 500 in accordance with exemplary embodiments. The method 500 can include preparation of the subject (e.g., eye or sample) for imaging 502, illumination of the subject 504, acquisition and storage of spectral data and associated polarization states from in or around the subject 506, calibration of the data, e.g., for media opacity 508, and comparison of spectral data with normative data (e.g., in a spectral library) for identification of clinically relevant diagnostic information 510, and electronic display of analyzed data 512. Such displayed data can further be used for diagnosis 514 of disease states in tissue, as indicated.

Preparation of the eye, sample or subject for imaging 502 can include preparing the target object (i.e., subject) for appropriate imaging as described below. For exemplary embodiments used for the imaging of the structures of the eye, preparation 502 can include but is not limited to: (a) pretreatment of the eye, sample or subject with agent(s) to improve clarity, transmissivity, or to otherwise alter spectral or anisotropy of ocular tissues. This can include use of material that may be injected intravenously, intraperitoneally, intraocularly, or administered topically, orally, parenterally or by suppository. For example, topical use of artificial tears or lubricants to improve corneal clarity and alter the anisotropic properties of the tear film. Preparation 502 can include administration of the noted material(s) for the purpose of changing any spectral or anisotropic property of target object (e.g., tissues) to obtain data for research, medical diagnostic or therapeutic purposes. Preparation 502 can also (or, in the alternative) include positioning of the target object (i.e., subject) to alter reflectance, transmittance, scatter or otherwise alter spectral or anisotropic properties for the purpose of localizing target tissue or to obtain data for research, medical diagnostic or therapeutic purposes. This can include, but is not limited to, use of head-rests, contact or non-contact lenses. For exemplary embodiments directed to the eye, preparation 502 can include use of contact or non-contact lenses on the surface of the eye, sample or subject for purposes of altering the spectral or anisotropic profile of target tissue or samples to obtain useful data for research, medical diagnostic or therapeutic purposes. Preparation 502 can include use of specific electromagnetic radiation (e.g., narrow-band light or laser light) to stimulate, suppress or otherwise alter spectral or anistropic properties of the subject to obtain useful data, e.g., for research, medical diagnostic or therapeutic purposes.

Illumination of the subject 504 can be achieved with any suitable type or types of light. Examples include broadband white light, laser light of any wavelength, filtered light, ultraviolet light, infrared light and/or a light having a defined wavelength range. Illumination 504 can originate from one or more sources and result in light being reflected from the sample, light being transmitted through the sample, light being emitted from the sample, and/or light being scattered from the sample. Such illumination can be continuous wave or pulsed or a combination of both. Illumination 504 can also be for the purpose of time averaged (continuous) or time-resolved recordings, e.g., as appropriate for the goal of the observation.

Continuing with the description of method 500, data acquisition 506 can include the simultaneous or sequential recording of one or more spatially registered spectra and associated polarization states from the subject (e.g., retina or sample). In the case of the eye, the subject or target area can include ocular structures including, but not limited to the tear film, cornea, aqueous humor, iris, lens, lens capsule, vitreous, retina (and various retinal layers), blood vessels, blood components, eye lids, eye lashes, lid margins, conjunctiva, sclera, extraocular muscles, trabecular meshwork, or any other structures located within or around the orbit. Data acquisition 506 may be done with any embodiment of a spectrometer, polarimeter or combination thereof which provides spatially registered data. Data acquisition can be achieved with any suitable detector or recording device including, but not limited to, a cooled high dynamic range CCD, an intensified CCD, video rate CCD, and/or a time-gated intensified CCD. Such CCD detectors can be configured as focal plane arrays (FPAs). Any suitable materials, e.g., semiconductor alloys, may be used to achieve detection of desired spectral ranges, e.g. any sub-range from UV through IR. Spectral data can refer to spectra that are reflected, refracted, transmitted, scattered, or emitted from target samples or tissues. Spectral and polarimetric data can be obtained from biological tissues in vivo or in vitro. For the purposes of calibration, e.g., as described in further detail below, spectral data can also be from non-biologic reference materials that are applied to the sample or delivered into the organism orally, parenterally (e.g., veins, arteries), rectally, transdermally, transurethral, intravitreal, intracameral, intraperitoneal, or other means. Such non-biologic materials can serve as spectral indicators ("contrast agents") of surrounding tissue conditions including but not limited to ion concentrations (sodium, potassium, chloride, calcium, iron, hydrogen, cobalt, nickel, silver, mercury, gold, zinc, silicone, selenium), pH, oxygen levels, carbon dioxide levels, phosphate levels, bicarbonate levels, hydroxide levels, carbon monoxide levels, temperature, and electromagnetic fields.

Acquired data, e.g., after tomographic reconstruction, can be stored as a hyperspectral cube where the x, y dimensions represent spatial information and z-axis represents spectral and/or polarization information. Alternative methods for data analysis and storage include any method utilizing a multidimensional data model and/or using any online analytical processing methods. Any suitable storage medium or media, e.g., hard disks, RAM, ROM, flash memory, optical discs, optical tape, etc., may be used for storage of such hyperspectral cube data.

Spectral information/data and/or spatially coregistered polarization information/data (e.g., of or derived from an image of a target ocular structure that is associated with an adjacent or intervening optical medium that may alter the optical properties of the target structure) acquired by any embodiment of a spectrometer, polarimeter or combination thereof may be calibrated 508 for deleterious optical effects (i.e., "optical noise" or "noise") of the ocular media. Such noise can be in addition to or influence spectral and/or polarization properties of light passing through or reflecting from a target ocular structure and recorded as an image, and can include fluorescence, anisotropy, absorption, scattering, and other known optical effects. Depending on the target of interest the sources of noise will vary.

Structures or optical media of relevance to calibration include but are not limited to tear film, cornea, aqueous humor, lens and lens capsule, vitreous humor, and internal limiting membrane; they can also include interstitial spaces (in the case of edema), an intraocular foreign body, an implanted device in the eye (e.g., a medical device such as a retinal prosthesis), an intraocular mass, a surgically placed material, a biological tissue, a fluorescently or chromatically labeled material or materials, and nanoparticles such as injected nanoparticles, and/or dyes, to list a few. Other structures or optical media may be imaged and calibrated within the scope of the present disclosure. It is important to note that the same structure or optical medium can be the target of interest in one case and the source of noise in another case, e.g., depending on the disease process. For example, a cataract may be the source of "spectral noise" when imaging the retina to evaluate for retinal disease; however, the cataract may also be a target tissue of interest if imaging the eye to evaluate for lens pathology.

Calibration for the ocular medium or media can be done in various ways. Exemplary embodiments of calibration are described below for FIGS. 6-8.

With continued reference to FIG. 5, after calibration 508 as described above, spectral data and associated polarization states may be analyzed for pathological changes. In order to identify pathologic changes, spectral and polarimetric data from a target tissue will be compared 510 with a normative spectral and polarimetric database of similar tissue. For this purpose, an average anisotropy, absorbance, transmission, scatter and/or intrinsic fluorescence spectrum may be determined for each normal tissue of interest in vitro (e.g., tear film, cornea, aqueous humor, lens, lens capsule, vitreous humor, internal limiting membrane, retinal pigment epithelium, choroid, blood vessels, blood, optic nerve, sclera, lamina cribrosa and retina). A compilation 510 of such data, e.g., ranging from the UV through the NIR from 300-2000 nm, can constitute a normative spectral and polarimetric database. Such a database may be the same in vitro database described previously or may be a database of normal tissue derived from a population of normal subjects or targets. For example, spectra from ischemic retina may be compared to a database of spectra and polarization values from normal retinal tissue. This comparison 510 can correct for normal variations in tissue anisotropy, pigmentation, vascularity, and other non-pathologic tissue changes. This comparison can be considered a form of data normalization to account for background noise from within the target tissue of interest. Normalization here refers to a difference calculation between spectra and anisotropy from target regions of interest and from non-target regions that have normal tissue (i.e., background spectra). For example, the normalization will reveal unique wavelengths and polarization states that characterize the ischemic tissue and not the normal, non-ischemic tissue. Normalization of data can occur in two forms.

Intrasample normalization may generally take the form of comparison of background signal to areas of possible pathology within the same sample or patient. When possible, normalization can be achieved using background spectra and polarization data from non-pathologic regions of the same eye that contains the target tissue. When this is not possible, background measurements from the contralateral eye can be used. Intersample normalization may generally take the form of comparison of a population average measurements (adjusted for age, race, sex, fundus pigmentation and lens opacification) to the target measurements from an individual sample or patient.

Either method of normalization can be designed to identify pathologic changes in the spectra and polarization states of the target tissue. Again, comparisons between and among samples may be made using a number of mathematical methods including classical least squares regression (CLS), inverse least squares regression (ILS), partial least squares regression (PLS), principal components regression (PCR), hierarchical cluster analysis (HCA), linear discriminant analysis (LDA) or a combination thereof.

Electronic display 512 of the above calibrated and corrected data may take the form of a pseudocolored or grayscale images on an appropriate device (computer screen, LCD, etc). Display 512 of this data may be in the operating room, outpatient or inpatient clinical setting. The displayed data/images may be used for diagnosis 514, e.g., of the presence of a disease organism.

Figure 6:
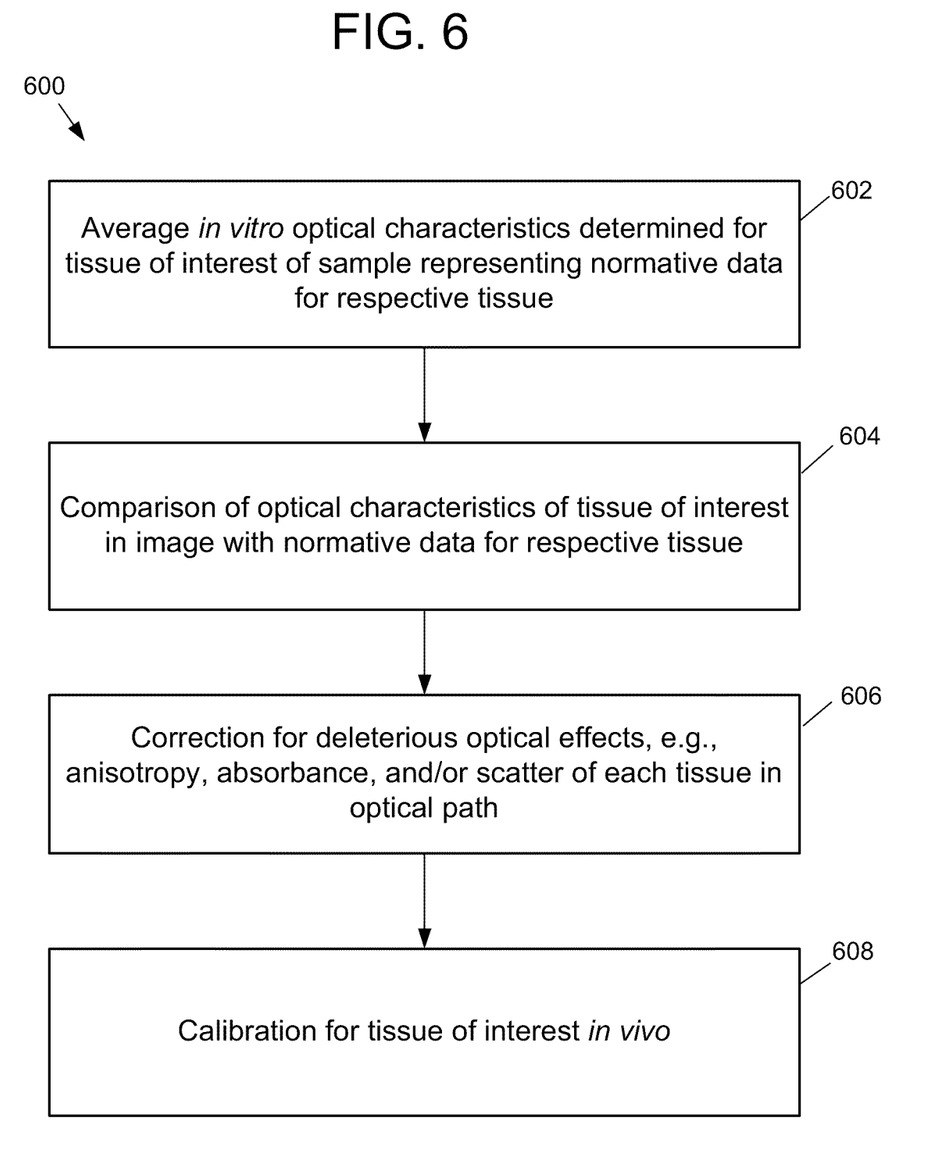
FIG. 6 depicts a flow chart of an example of a method of calibration.

FIG. 6 depicts a flow chart for a method of calibration 600, in accordance with exemplary embodiments. Calibration method 600 can be accomplished by correction of spectral data and polarization states for the effects of individual ocular media components. For this purpose, an average anisotropy, absorbance, transmission and/or intrinsic fluorescence spectrum can be determined for each tissue of interest in vitro (e.g. tear film, cornea, aqueous humor, lens and lens capsule, vitreous, tissue hydration (edema) and internal limiting membrane), as described at 602. A compilation of such data ranging from, e.g., 300-2000 nm can constitute or be used as a normative spectral and polarimetric database. An image of a target of interest, e.g., a retina, can be compared to the normative data 604. Deleterious optical effects of each tissue type in the optical path shown in the image can be removed, as described at 606. Calibration 608 of target spectra in vivo can be thereby be achieved, correcting for the anisotropy, absorbance and scatter of each tissue in the optical path. Such corrections may be based on any of a number of mathematical methods.

Examples of suitable mathematical models include but are not limited to classical least squares regression (CLS), inverse least squares regression (ILS), partial least squares regression (PLS), principal components regression (PCR), hierarchical cluster analysis (HCA), linear discriminant analysis (LDA) or a combination thereof.

Figure 7:
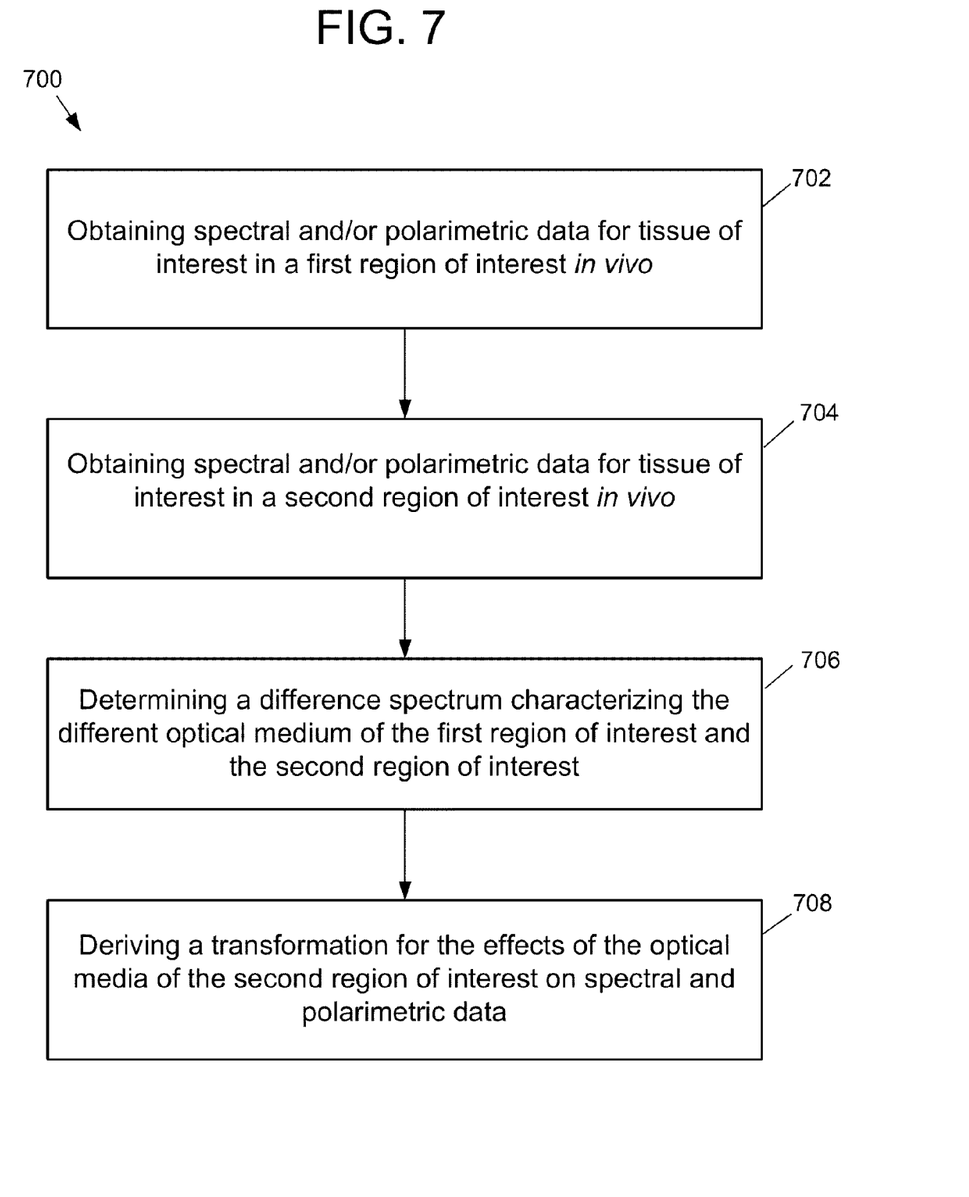
FIG. 7 depicts a flow chart of an example of a further method of calibration.

Another method for calibration of spectral data and associated polarization states is achieved by correcting for the aggregate effect of ocular media in vivo. FIG. 7 depicts a flow chart for a further method of calibration 700, in accordance with exemplary embodiments. Spectral and/or polarimetric data of a well-characterized spectral and polarizing target at first region of interest 702 (e.g., in vivo outside the eye) can be compared with substantially the same target in a second region of interest 704 (e.g., inside the eye). For example, tissues inside and outside the eye are very different, however, blood vessels and the constituents of blood itself are substantially similar throughout the body, varying mainly in oxygen concentration between arteries and veins. Therefore, comparison of the spectra and polarization properties of normal arterial blood from outside of the eye (e.g., conjunctival or episcleral vessels) to arterial blood inside the eye (e.g., iris vessels, retinal vessels and choroidal vessels) will allow a difference spectrum to be identified (described at 706) that is largely due to the effect of the intraocular media on the spectra and polarization data. A similar difference spectrum can be generated for venous blood inside and outside the eye. This difference spectrum can be characterized at any or all wavelengths from, e.g., 300-2000 nm. Based on this difference spectrum, an empiric transformation can be derived (as described at 708) for the effects of the intraocular media on the spectral and polarimetric data.

Such comparisons and calculations can be made using a number of mathematical methods. Examples of suitable mathematical models include but are not limited to including classical least squares regression (CLS), inverse least squares regression (ILS), partial least squares regression (PLS), principal components regression (PCR), hierarchical cluster analysis (HCA), linear discriminant analysis (LDA) or a combination thereof.

Figure 8:
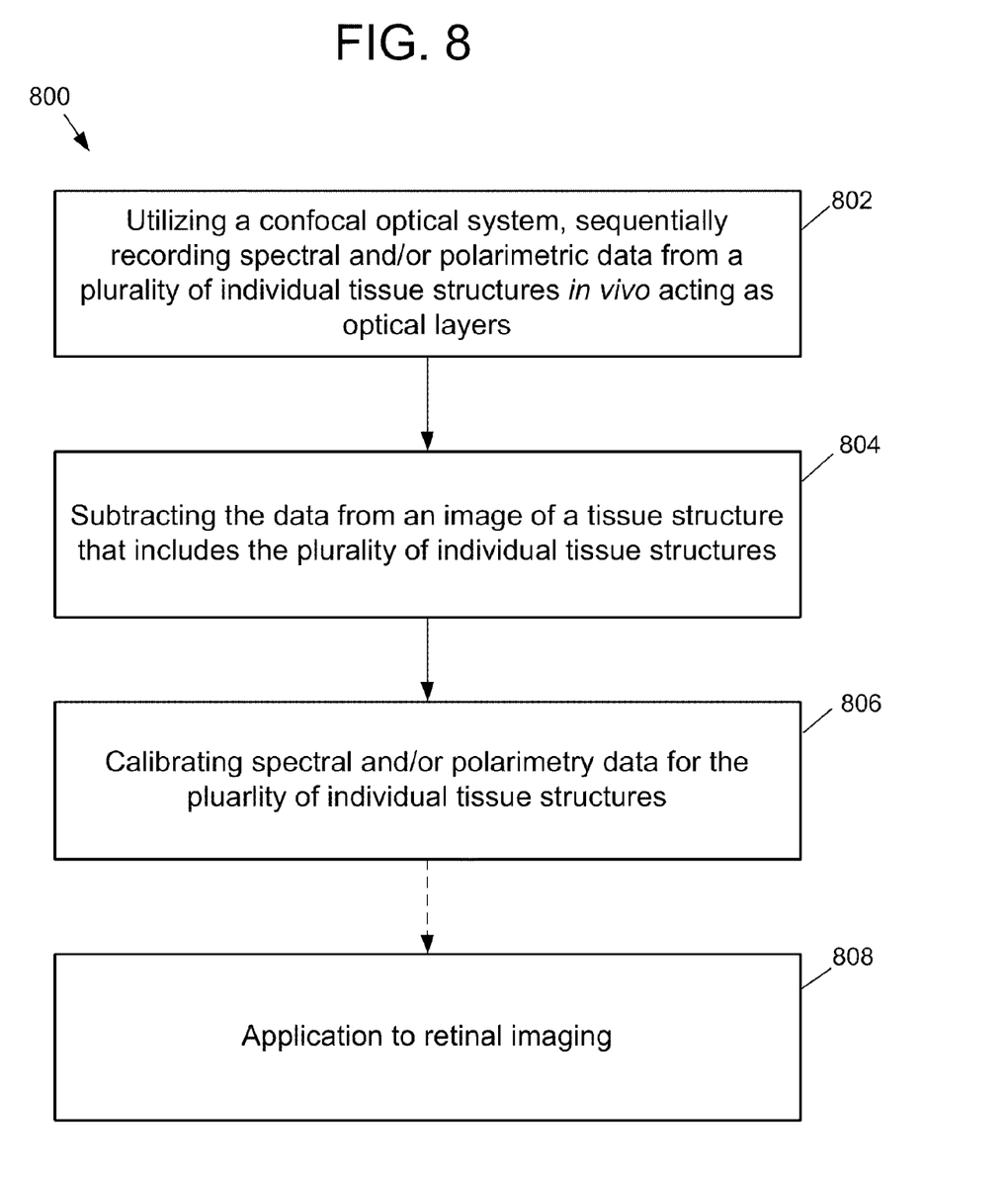
FIG. 8 depicts a flow chart of an example of a further method of calibration.

Another method for calibration of spectra and associated polarization states may be achieved by adapting a confocal optical system. FIG. 8 depicts a flow chart for such a method of calibration 800, in accordance with exemplary embodiments. For method 800, a confocal optical system can be adapted and used sequentially record spectral and/or polarimetric data from individual optical layers/elements of the eye, as described at 802. This data can be subtracted from an image, e.g., of a retina, as described at 804. For example, confocal spectra and polarimetry from the tear film, cornea, aqueous humor, lens, lens capsule, vitreous, and internal limiting membrane may be sequentially acquired and then subtracted from a hyperspectral image (e.g., image 2 of FIG. 3) of the retina. This would allow for calibration of the hyperspectral retinal image for any "noise" from the ocular media. This calibration may be characterized at desired wavelengths, e.g., any or all wavelengths from 300-2000 nm.

For an embodiment of method 800, a pinhole calibration image from a fundus camera can be used. Each image can be focused on successive layers of ocular media as mentioned above and subtracted from the final image of the retinal target scene. Such comparisons and calculations can be made using a number of mathematical methods including classical least squares regression (CLS), inverse least squares regression (ILS), partial least squares regression (PLS), principal components regression (PCR), hierarchical cluster analysis (HCA), linear discriminant analysis (LDA) or a combination thereof.

Figure 9:
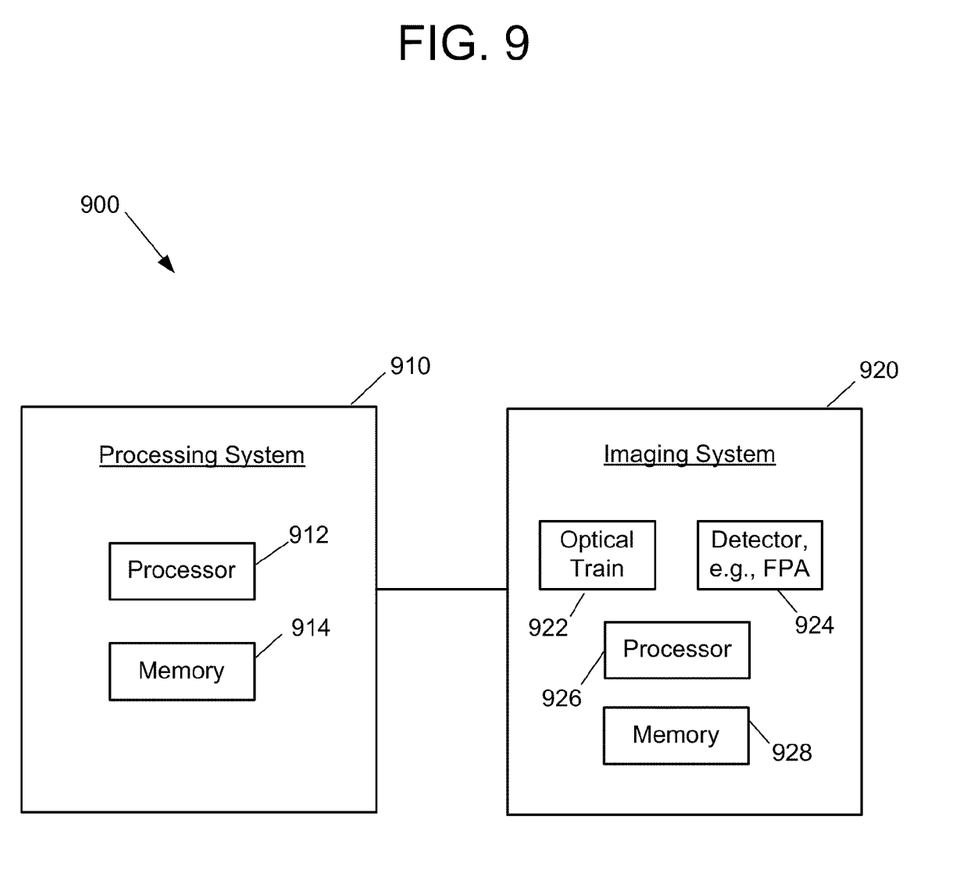
FIG. 9 depicts a diagram of an example of a calibration system.

FIG. 9 depicts a diagram of a calibration system 900, in accordance with exemplary embodiments. System 900 can include a processing system 910 with a processor (or multiple processors) 912 and memory suitable for image processing. In some embodiments, calibration system 900 can include an imaging system 920 with an optical train 922, a detector 924, a processor 926, and memory 928. In exemplary embodiments, imaging system 924 can include all of the components of a combined imaging spectrometer-polarimeter systems according to the present disclosure, e.g., systems 100A-100B of FIGS. 1A-1B. or system 300 of FIG. 3. Alternatively stated, in exemplary embodiments combined imaging spectrometer-polarimeter systems according to the present disclosure can perform and be used to perform calibration methods according to the disclosure.

In exemplary embodiments, calibration system 900 can be used to perform methods of the present disclosure, e.g., methods 600, 700, and/or 800 of FIGS. 6-8. In exemplary embodiments, processing system 910 and/or processor(s) 912 can include or run software or code including computer readable instructions for carrying out or performing methods or steps of methods of the present disclosure, e.g., methods 600, 700, and/or 800 of FIGS. 6-8, or step 508 of method 500. In exemplary embodiments, calibration system 900 can receive an image or data representing an image from combined imaging spectrometer-polarimeter systems according to the present disclosure, e.g., system 300 of FIG. 3.

The following examples of exemplary embodiments are set forth for increased ease or comprehension of the disclosure.

Example 1

An exemplary embodiment of the present disclosure is directed to a low cost diagnostic test for malaria detection. The test may be based on a portable, non-invasive, reusable and rapid retinal imaging technology that can detect malaria infection without the need for any laboratory tests. A snaphot hyperspectral-polarimetry camera can be used. In exemplary embodiments, the camera is adapted to a hand-held device for the field. The retina is the ideal site for evaluation of infection because it provides key advantages in detecting *Plasmodium* infection and evaluating the clinical course of the disease. The very high blood flow in the choroid provides a high signal-to-noise tissue source for spectral analysis of infected red blood cells. Unlike skin or the nail bed, the relatively clear ocular media minimize signal attenuation. In addition, the retina may serve as a proxy site for detection of cerebral malaria before the onset of potentially lethal central nervous system (CNS) involvement. Portable retinal imaging devices can eliminate the need for laboratory analysis of body fluids and allow screening of patients in remote locations. In addition, portable retinal imaging technology can be used in hospital and clinic based settings for rapid screening of patients without the need for blood samples.

Malaria infection begins with the bite of the female Anopheles mosquito and progresses through the many stages of the *falciparum* lifecycle. The intraerythrocytic stages of the parasitic lifecycle include development from an early ring stage to the trophozoite phase and finally to a schizont stage where the parasite replicates. During the trophozoite stage the parasite digests large quantities of hemoglobin and releases free ferrous protoporphyrin IX and denatured globin into the cell. The protoporphyrin IX is oxidized and then aggregates into an insoluble biomineral known as hemozoin. The intraparasitic heme concentration can be as high as 0.4M as the released heme moiety from the broken down hemoglobin is sequestered in the form of insoluble hemazoin in the *Plasmodium* food vacuoles. Under physiological conditions hemozoin remains insoluble and undegraded thus providing a molecular signature of infection. Raman spectroscopy can be used to grossly detect hemazoin in fixed cells and to localize hemazoin within RBCs. The Raman spectra of hemozoin show very intense signals and good signal to noise ratio with select excitation wavelengths such as 633 nm. Similar studies have been performed using synchrotron FT-IR microscopy, and direct ultraviolet laser desorption time-of-flight mass spectrometry. With the use of principal components analysis (PCA) investigators have been able to differentiate between the intraerythrocytic stages of the parasitic lifecycle based on the molecular signatures of hemazoin and specific lipid markers associated with hemazoin formation. Unfortunately, these imaging methodologies require substantial resources of hardware and laboratory support and are not suited for deployment in the field.

The spectral imaging system described herein can use the spectral signatures of hemoglobin and hemazoin to diagnose malaria infection in vivo by high-density spectral imaging of the retina with relatively minimal hardware.

The spectral imaging system described herein can use the spectral properties of hemoglobin for detection of oxy- and deoxyhemoglobin to qualitatively and quantitatively determine blood oxygen saturation in animal models as well as humans with retinal vascular disease (like diabetes, central retinal vein occlusion or central retinal artery occlusion).

A snapshot hyperspectral camera, in accordance with the present disclosure, can be used for diagnosis of disease states, e.g., malaria. The snapshot hyperspectral camera can be a simple attachment to a standard fundus camera used in everyday ophthalmology practices. The snapshot hyperspectral camera can capture spatial, spectral, and polarimetry information by imaging a scene through a two-dimensional grating which records multiple spectrally dispersed images of the retina. The camera can be mounted on a standard fundus camera and can acquire images containing approximately 50 wavelengths of spectral data in <3 msec. Consequently, hyperspectral images are minimally blurred by eye movements and do not need image registration to eliminate motion artifact or pixel misregistration. Data can be collected on a computer using standard image acquisition software. Computed tomographic algorithms are used to reconstruct the spectrally dispersed images into a "hyperspectral cube" of spectral and spatial information that can be probed for spectral information. This technology may be applied to detect malarial infection by simple photography of experimentally infected red blood cells in an experimental model eye and subsequently in animal models of disease. The spectral signatures of *Plasmodium falciparum* infected cells may be isolated as described below.

An in vitro system of *Plasmodium* infection can be used. *Plasmodium* organisms can be maintained in continuous culture using human erythrocytes. Infected red blood cells (RBC) can be imaged live in culture and in an artificial eye with glass capillaries that simulate retinal vessels. CTIS images can be taken of both infected and uninfected RBCs and images can be analyzed for difference signals that are representative of spectral signatures of hemazoin and hemoglobin species. Control spectra of hemozoin may be obtained using synthetic hemozoin (Beta-hematin). Data collection can identify the spectral signatures of hemazoin as well as concomitant changes in oxy/deoxyhemoglobin species that are known to be characteristic of *Plasmodium* infection. For verification, infected RBCs may be injected into anesthetized animals while simultaneous imaging of the retina is performed with the CTIS camera. Comparison of the baseline non-infected CTIS images and infected images can allow demonstration of detection of blood borne infection in vivo without having to develop a complicated model of infection through the natural mechanisms of disease. An exemplary embodiment can include a small hand-held hyperspectral unit that can be deployed for field use.

Example 2

It was found for a tested embodiment that using the color image as the initial condition for the reconstructions significantly reduces reconstruction time by decreasing the number of iterations required. This may be due to the fact that the color image already contains some spectral information as the initial "guess." A Zeiss ff450+ fundus camera was used as the objective assembly to image the retina of the human test subjects. Any suitable fundus camera may be used. Examples of suitable fundus camera systems include those made commercially available by the following companies: Topcon, Zeiss, Canon, Nidek, and Kowa. National Institute of Standards and Technology (NIST) traceable reflectance color targets were used to verify the accuracy of the CTIS reconstruction process. Comparison of the CTIS spectral reflectance shows agreement to the NIST standards within a few percent over 450 to 750 nm.

In the tested embodiment, a filter matched to the camera flash bulb spectra optimized the dynamic range of the silicon detector from 500 to 600 nm. The fundus objective had a large 24×36 mm image plane. Demagnification (1/7.2×) was needed in order to compensate for this large size and was accomplished using a 2× tele-extender along with a 180-mm commercial-off-the-shelf (COTS) lens assembly for collimation. The field stop was set at 11×11 mm and combined with a 50-mm COTS reimaging lens reduced the field of view to 18 deg with a Fundus camera setting of 50 deg, with minimal vignetting. This field of view converted to an image plane at the detector across 208×208 pixels. The Fundus camera had three different settings for the field of view and each maps a higher resolution image across the pixel space of the zeroth order CTIS. The Fundus camera settings of 50, 30, and 20 deg correspond to 18, 10.8, and 7.2 deg, respectively.

Accordingly, a combined imaging spectrometer-polarimeter according to the present disclosure may have applications ranging from material sciences to biological and medical sciences. In exemplary embodiments, a spectrometer-polarimeter can allow for improved diagnosis, monitoring and treatment of retinal diseases including but not limited to retinal vascular disease, macular degeneration, glaucoma, retinal dystrophy, retinal degenerations, vitreous syneresis, vitreous hemorrhage, uveitis, retinal nevi and melanoma. Techniques (methods and/or systems) of the present disclosure may also be useful for acquisition, storage and calibration of spectroscopic and polarimetric data from humans or animals in vivo for other diagnostic and therapeutic applications. For example, methods of the present disclosure can be applicable for acquisition and calibration of spectral information obtained by microscopy, fundus photography, indirect ophthalmoscopy, direct ophthalmoscopy, video or photographic endoscopy or laparoscopy, and the like. Such techniques can be applied to any device which illuminates, acquires and stores spatially registered spectral and polarization information, simultaneously.

The components, steps, features, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits and advantages. These also include embodiments in which the components and/or steps are arranged and/or ordered differently.

In reading the present disclosure, one skilled in the art will appreciate that embodiments of the present disclosure can be implemented in hardware, software, firmware, or any combinations of such, and over one or more networks. Suitable software can include computer-readable or machine-readable instructions for performing methods and techniques (and portions thereof) of designing and/or controlling the implementation of data acquisition and/or data manipulation. Any suitable software language (machine-dependent or machine-independent) may be utilized. Moreover, embodiments of the present disclosure can be included in or carried by various signals, e.g., as transmitted over a wireless RF or IR communications link or downloaded from the Internet.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications which have been cited in this disclosure are hereby incorporated herein by reference.

The phrase "means for" when used in a claim is intended to and should be interpreted to embrace the corresponding structures and materials that have been described and their equivalents. Similarly, the phrase "step for" when used in a claim embraces the corresponding acts that have been described and their equivalents. The absence of these phrases means that the claim is not intended to and should not be interpreted to be limited to any of the corresponding structures, materials, or acts or to their equivalents.

Nothing that has been stated or illustrated is intended or should be interpreted to cause a dedication of any component, step, feature, benefit, advantage, or equivalent to the public, regardless of whether it is recited in the claims.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

What is claimed is:

1. A snapshot imaging spectrometer-polarimeter system for capturing simultaneous spectral and spatially colocalized polarization states from an image of ocular structure, the system comprising:
    one or more focal plane array detectors configured to detect light of one or more selected wavelength ranges;
    a fundus camera adapted to receive an image of ocular structure, and including a primary imaging lens and one or more collimating lenses configured along an optical path and to receive the image and focus the image on the one or more focal plane array detectors;
    a dispersive optical element configured along the optical path and to disperse the image in two dimensions;
    one or more polarizers configured along the optical path;
    one or more retarders configured along the optical path;
    an acquisition system configured to collect spectral and polarization data from the one or more focal plane array detectors; and
    a processing system operative to receive, from the acquisition system, data representing an image of the ocular structure and to calibrate the image for deleterious optical effects of biological optical media represented within the image.

2. The system of claim 1, wherein the image includes, tissue, an implanted device, injected nanoparticles or dye.

3. The system of claim 1, further comprising a field stop aperture configured to limit a field of view of the system.

4. The system of claim 1, further comprising one or more illumination sources configured to direct light of a desired spectrum and/or polarity along the optical path.

5. The system of claim 1, wherein one of the one or more focal plane array detectors comprises a transmissive filter adapted to perform a user-identified transmissive function, the transmissive filter positioned over the focal plane array detector.

6. The system of claim 1, wherein one of the one or more the focal plane array detectors comprises a transmissive filter adapted to perform a user-identified transmissive function, the transmissive filter positioned over the illumination source.

7. The system of claim 1, wherein the dispersive element comprises a 2D diffraction grating.

8. The system of claim 1, wherein one of the one or more focal plane array detectors comprises a digital image sensor comprising three areas of pixels on a detector, the three areas of detectors comprising one area of detectors configured to detect red light, one area of detectors configured to detect green light, and one area of detectors configured to detect blue light.

9. The system of claim 1, wherein one of the one or more focal plane array detectors comprises a monochromatic focal plane array detector.

10. The system of claim 1, further comprising a fundus camera configured to provide an image to the collimating lens.

11. The system of claim 1, further comprising a confocal imaging device configured to provide an image to the one or more focal plane array detectors.

12. The system of claim 11, wherein the confocal imaging device comprises a confocal scanning laser ophthalmoscope.

13. The system of claim 1, further comprising an optical coherence tomographic device configured to provide an image to the one or more focal plane array detectors.

14. The system of claim 1, further comprising an endoscopic or laparoscopic camera configured to provide an image to the one or more focal plane array detectors.

15. The system of claim 14, wherein the endoscopic camera is configured with an intraocular camera.

16. The system of claim 1, wherein the one or more polarizers and one or more retarders are configured as a Mueller matrix imaging polarimeter (MMIP) configured to determine a partial or complete polarization aberration matrix of the image.

17. The system of claim 1, wherein the one or more focal plane detector arrays comprise a single focal plane detector array.

18. The system of claim 1, wherein the one or more focal plane detector arrays comprise a first focal plane detector array configured to detect wavelength data of the image and a second focal plane detector array configured to detect polarization state data of the image, wherein the first focal plane detector array and the second focal plane detector array have spatially coregistered outputs.

19. The system of claim 1, wherein the spectral information from the target scene is spatially coregistered with the polarization states from the scene by a system-transfer calibration matrix.

20. The system of claim 1, further comprising a display configured to display representations of the image.

21. The system of claim 1, wherein the system is further configured to (i) receive average in vitro optical characteristic data as normative data for tissue of interest shown in the image, (ii) compare data or optical characteristics of tissue of interest in the image with normative data for respective tissue, (iii) correct the image by removing deleterious optical effects of the tissue as indicated in the normative data for the tissue of interest.

22. The system of claim 1, wherein the system is further configured to (i) receive data of in vivo optical characteristics for a tissue of interest, (ii) compare data of optical characteristics of a target tissue of interest shown in the image with the received data in (i), (iii) determine a difference spectrum representing an optical medium shown in the image, and (iv) based on the difference spectrum, correct the image.

23. The system of claim 1, wherein the system is further configured to (i) receive data of in vivo optical characteristics for each of a plurality of tissues of interest along an optical path shown in the image, (ii) subtract data obtained in (i) from the image with the received data in (i).

24. The system of claim 1, wherein the deleterious optical effects include anisotropy.

25. The system of claim 1, wherein the deleterious optical effects include absorbance.

26. The system of claim 1, wherein the deleterious optical effects include target fluorescence.

27. The system of claim 1, wherein the deleterious optical effects include scattering.

28. The system of claim 1, further comprising an imaging system configured to produce an image of a region of interest and provide data representing the image to the processing system.

29. The system of claim 28, wherein the imaging system comprises a spectrometer.

30. The system of claim 28, wherein the imaging system comprises a polarimeter.

31. The system of claim 28, wherein the imaging system comprises a confocal optical system.

32. The system of claim 28, wherein the processing system comprises a processor and memory.

33. The system of claim 28, further comprising a display configured to display a representation of the image.

34. A method of calibrating an image of an ocular structure including an optical medium, the method comprising:
receiving combined spectral and polarization data, wherein the data are derived from an image of an ocular structure having an optical medium, that is generated using the snapshot imaging spectrometer-polarimeter system of claim 1; and
removing deleterious optical effects of the ocular media from the data, and calibrating the image for deleterious optical effects of the ocular media.

35. The method of claim 34, further comprising receiving spatially coregistered spectral data from a spectrometer.

36. The method of claim 34, further comprising receiving spatially coregistered polarization data derived from the image.

37. The method of claim 36, further comprising receiving polarization data from a polarimeter.

38. An article of manufacture comprising:
a non-transitory machine readable storage medium; and
executable program instructions embodied in the machine readable storage medium that, when executed by a processor of a programmable computing device, configures the programmable computing device to control the acquisition system of claim 1 receiving an image of an ocular structure including an optical medium, to perform functions for calibrating the image for optical noise, including instructions to:
remove deleterious optical effects of the ocular medium from the data, and calibrate the image for deleterious optical effects of the ocular medium.

39. The article of manufacture of claim 38, further comprising instructions for receiving spectral data from a spectrometer.

40. The article of manufacture of claim 38, further comprising instructions for receiving spatially coregistered polarization data derived from the image.

41. The article of manufacture of claim 40, further comprising instructions for receiving polarization data from a polarimeter.

42. The article of manufacture of claim 38, further comprising instructions for focusing a camera on or in an eye for obtaining the image.

43. The article of manufacture of claim 38, further comprising instructions for tomographic reconstruction of the image into a hyperspectral cube.

* * * * *